(12) United States Patent
Vanderzande et al.

(10) Patent No.: US 7,087,787 B1
(45) Date of Patent: Aug. 8, 2006

(54) METHOD FOR PRODUCING DERIVATIVES OF 4-ALKYLSULFINYL METHYLARYLENE METHANOLS

(75) Inventors: Dirk Vanderzande, Bilzen (BE); Joanes Gelan, Genk (BE); Albert van Breemen, Eindhoven (NL); Michael Van Der Borght, Turnhout (BE); Laurence Lutsen, Coudekerque-Branche (FR); Raf Kiebooms, Genk (DE); Willi Kreuder, Mainz (DE)

(73) Assignee: Covion Organic Semiconductors GmbH, Frankfurt (DE)

( * ) Notice: Subject to any disclaimer, the term of this patent is extended or adjusted under 35 U.S.C. 154(b) by 0 days.

(21) Appl. No.: 09/786,581

(22) PCT Filed: Aug. 27, 1999

(86) PCT No.: PCT/EP99/06324

§ 371 (c)(1),
(2), (4) Date: Aug. 9, 2001

(87) PCT Pub. No.: WO00/14059

PCT Pub. Date: Mar. 16, 2000

(30) Foreign Application Priority Data

Sep. 8, 1998 (DE) ............................... 198 40 943

(51) Int. Cl.
*C07C 321/00* (2006.01)
*C07D 333/16* (2006.01)

(52) U.S. Cl. .......................................... 568/21; 549/78
(58) Field of Classification Search ................ 549/78; 568/21

See application file for complete search history.

(56) References Cited

U.S. PATENT DOCUMENTS

| | | | | |
|---|---|---|---|---|
| 2,965,649 A * | 12/1960 | Johnston | ...................... | 549/14 |
| 3,172,862 A | 3/1965 | Gumee et al. | ......... | 252/301.16 |
| 3,836,385 A * | 9/1974 | Schmidt et al. | .............. | 427/302 |
| 4,054,578 A * | 10/1977 | Frenier et al. | ................. | 549/13 |
| 4,210,552 A * | 7/1980 | Frenier et al. | .............. | 510/260 |
| 5,525,736 A * | 6/1996 | Nystrom et al. | ................ | 549/5 |
| 5,763,539 A | 6/1998 | Stern et al. | .................. | 525/535 |
| 5,777,070 A | 7/1998 | Inbasekaran et al. | | |
| 5,917,003 A | 6/1999 | Gelan et al. | ................. | 528/330 |
| 6,908,722 B1 * | 6/2005 | Ebata et al. | .............. | 430/270.1 |

FOREIGN PATENT DOCUMENTS

| | | |
|---|---|---|
| EP | 0 167 139 | 1/1986 |
| EP | 0 170 073 | 2/1986 |
| EP | 0 423 283 | 1/1995 |
| EP | 0 644 217 A1 | 3/1995 |
| EP | 0 443 861 | 7/1995 |
| EP | 0 705 857 A2 | 9/1995 |
| GB | 2 313 127 A | 11/1997 |
| JP | 02250836 | 10/1990 |
| WO | WO 97/05184 | 2/1997 |
| WO | WO 97/33323 | 9/1997 |

OTHER PUBLICATIONS

Lahti, et al., Polymerization of a,á-Bis (dialkylsulfonio)-p-xylene Dihalides via p-Xylylene Intermediates: Evidence for a Nonradical Mechanism, *J. Am. Chem. Soc.*, 110, 7258-7259 (1988).
Burn, et al., Chemical Tuning of the Electronic Properties of Poly(p-phenylenevinylene)-Based Copolymers, *J. Am. Chem. Soc.*, 115, 10117-10124 (1993).
Issaris, et al., Polymerization Mechanism of 1-[(Butylsufi(o)nyl)methyl]-4-(halomethyl)benzene: The Effect of Polarizer and Leaving Group, *Macromolecules*, 31, 4426-4431 (1998).
van Breemen, et al., Highly Selective Route for Producing Unsymmetrically Substituted Monomers toward Synthesis of Conjugated Polymers Derived from Poly (p-phenylene vinylene), *J. Org. Chem.*, 64, 3106-3112 (1999).
International Search Report for PCT/EP99/06324.
Luettringhaus, et al., *Arznelmittel Forsch.*, 13, 366 (1963).
Luettringhaus, et al., *Justus Liebigs Ann. Chem.* 671, 165-196 (1964).
Bardsley, et al., *Biochem. J.*, 128, 253-6 (1972).
Antoun, *Collect. Czech. Chem. Commun.*, 52, 1, 162 (1987).
Jin, et al., *J. Chem. Soc. Chem. Commun.*, 17, 1205 (1989).
Brooke, et al., *J. Fluorine Chem.*, 50, 1, 101 (1990).
Burn, et al., *J. Chem. Soc. Perkin Trans.*, 1,23, 3225 (1992).
Sonoda, et al., *Bull. Chem. Soc. Jpn.*, 65, 3, 853 (1992).
Lee, et al., *Mol. Cryst. Liq. Cryst. Sci. Technol.*, Sect. A, 247, 121 (1994).
Hwang, *J. Chem. Soc. Chem. Commun.*, 21, 2461 (1994).
Stenger-Smith, et al., *J. Org. Chem.*, 59, 20, 6107 (1994).
Salbeck, et al., *Phys. Chem.*, 100, 1667, (1996).
Hwang, et al., *Mol. Cryst. Lig. Cryst. Sci. Technol.*, Sect. A,280, 39 and 175 and 181 (1996).
March, *Adv. Org. Chem.*, 3rd Edn., J. Wiley, New York, pp. 1089-1090.

* cited by examiner

*Primary Examiner*—Deborah C. Lambkin
(74) *Attorney, Agent, or Firm*—Connolly Bove Lodge & Hutz LLP

(57) ABSTRACT

The invention relates to a method for producing derivatives of 4-alkylsulfinyl methylarylene methanols. Derivatives of 4-alkylsulfinyl methylarylene methanols are valuable monomers in the production of conjugated polymers, which are suitable for use as electroluminescent materials.

34 Claims, No Drawings

METHOD FOR PRODUCING DERIVATIVES OF 4-ALKYLSULFINYL METHYLARYLENE METHANOLS

The present invention relates to a process for the preparation of derivatives of 4-alkylsulfinylmethylarylenemethanol. Derivatives of 4-alkylsulfinylmethylarylenemethanol are valuable monomers in the preparation of conjugated polymers, which are suitable, inter alia, as electroluminescent materials.

There is considerable industrial demand for large-area solid-state light sources for a number of applications, predominantly in the area of display elements, display-screen technology and illumination technology. The requirements made of these light sources cannot at present be completely satisfied by any of the existing technologies.

As an alternative to conventional display and illumination elements, such as incandescent lamps, gas-discharge lamps and non-self-illuminating liquid-crystal display elements, electroluminescent (EL) materials and devices, such as light-emitting diodes (LEDs), have already been in use for some time.

Besides inorganic electroluminescent materials and devices, low-molecular-weight, organic electroluminescent materials and devices have also been known for about 30 years (see, for example, U.S. Pat. No. 3,172,862). Until recently, however, such devices were greatly limited in their practical applicability.

EP-A-0 423 283 and EP-A-0 443 861 describe electroluminescent devices which contain a film of a conjugated polymer as light-emitting layer (semiconductor layer). Such devices offer numerous advantages, such as the possibility of manufacturing large-area, flexible displays simply and inexpensively. In contrast to liquid-crystal displays, electroluminescent displays are self-illuminating and therefore do not require an additional illumination source at the back.

A typical device in accordance with EP-A-0 423 283 consists of a light-emitting layer in the form of a thin, dense polymer film (semiconductor layer) containing at least one conjugated polymer. A first contact layer is in contact with a first surface, and a second contact layer is in contact with a further surface of the semiconductor layer. The polymer film of the semiconductor layer has a sufficiently low concentration of extrinsic charge carriers so that, on application of an electric field between the two contact layers, charge carriers are introduced into the semiconductor layer, the first contact layer becoming positive compared with the other layer, and the semiconductor layer emits radiation. The polymers used in such devices are conjugated. The term "conjugated polymer" is taken to mean a polymer which has a delocalized electron system along the main chain. The delocalized electron system gives the polymer semiconductor properties and enables it to transport positive and/or negative charge carriers with high mobility.

EP-A-0 423 283 and EP-A-0 443 861 describe poly(p-phenylenevinylene) as polymeric material for the light-emitting layer. This can be modified by alkyl, alkoxy, halogen or nitro substituents on the aromatic ring. Such polymers have since then been investigated in a large number of studies, and dialkoxy-substituted PPVs in particular have already been optimized to a considerable extent toward the market introduction stage (cf., for example, J. Salbeck, Ber. Bunsenges. Phys. Chem. 1996, 100, 1667). However, the development of such polymers can in no way be regarded as complete. Thus, inter alia, improvements are still necessary regarding the service life, stability and also the achievable color. For example, the above polymer class which has been developed the furthest, dialkoxy-PPVs, is only suitable for emission of orange-red light.

The above polymers require on the one hand high-purity monomers and also very complex monomers. Some of these monomers units are only accessible in the requisite quality by complex methods and must furthermore be purified by chromatography after their complex preparation.

There is therefore a great demand for processes for the preparation of corresponding monomer units in which the monomers are obtained in such a quality that chromatographic purification is unnecessary.

The present invention relates to a process for the preparation of compounds of the formula (I)

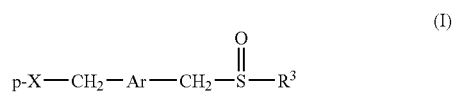

in which

Ar is an aromatic ring system having 4 to 20 carbon atoms, which may, if desired, be monosubstituted or polysubstituted by $C_1$–$C_{20}$-alkyl, $C_3$–$C_{20}$-alkoxy, $C_3$–$C_{20}$-branched alkyl, phenyl or benzyl radicals and which may contain up to 4 heteroatoms from the group consisting of oxygen, sulfur and nitrogen in the aromatic ring system, X is a leaving group, and R is unbranched alkyl having 1 to 20 carbon atoms, branched alkyl having 3 to 20 carbon atoms, cyclic alkyl, such as cyclohexyl, or $C_1$–$C_4$-alkyl-substituted cyclic alkyl, such as cyclohexylmethyl, phenyl or benzyl, which may be substituted or unsubstituted and/or contain heteroatoms, such as O, N and Si, comprising the following measures:

a) reaction of a compound of the formula (II)

in which Ar and X are as defined under the formula (I), with an organic sulfide of the formula (III)

in which $R^4$ and $R^5$ are identical or different and are unbranched alkyl having 1 to 20 carbon atoms, branched alkyl having 3 to 20 carbon atoms, cyclic alkyl having 3 to 10 carbon atoms, such as cyclobutyl, cyclopentyl or cyclohexyl, or $C_1$–$C_4$-alkyl-substituted cyclic alkyl, such as cyclohexylmethyl, or $R^4$ and $R^5$ together form a ring, which may also contain one or more heteroatoms selected from the group consisting of oxygen, sulfur and nitrogen, to give a compound of the formula (IV)

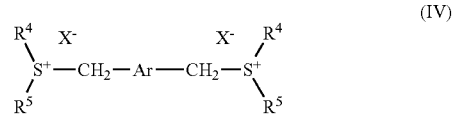

in which $R^4$, $R^5$, X and Ar are as defined above, b) reaction of the compound of the formula (IV) with from 0.85 to 1.1 equivalents of a mercaptan of the formula (V)

in which

R³ is unbranched alkyl having 1 to 20 carbon atoms, branched alkyl having 3 to 20 carbon atoms, cyclic alkyl, such as cyclohexyl, or C₁–C₄-alkyl-substituted cyclic alkyl, such as cyclohexylmethyl, phenyl or benzyl, which may be substituted or unsubstituted and/or contain heteroatoms, such as O, N and Si, to give a compound of the formula (VI)

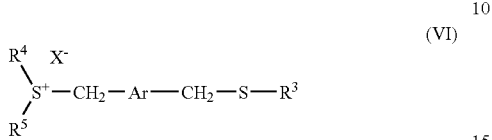

c) warming of the compound of the formula (VI) in a liquid and formation of the compound of the formula (VII)

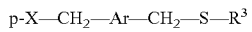

by elimination of an organic sulfide of the formula (III), where the compound of the formula (VII) is dissolved in the above liquid, d) oxidation of the compound of the formula (VII) using an oxidant, to give the compound of the formula (I).

The radical X is preferably a leaving group, such as halogen, —O-tosylate, —O-mesylate or —O-trifluoroacetate.

In the formula (I), p denotes para in respect of the two methylene radicals —CH₂— on both sides of the radical Ar.

The process according to the invention is preferably used for the preparation of compounds of the formula (I) in which Ar is the structural unit

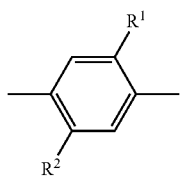

in which

R¹ and R² are identical or different and are hydrogen, an unbranched alkyl or alkoxy radical having 1 to 20 carbon atoms, a branched alkyl or alkoxy radical having 3 to 20 carbon atoms, phenyl or benzyl, where the abovementioned radicals may be unsubstituted or substituted by halogen, in particular chlorine, bromine or fluorine, cyano, nitro, or an ester having 1 to 20 carbon atoms.

Particular preference is given to compounds of the formula (I) in which Ar is as defined above, and R¹ and R², independently of one another, are an unbranched alkoxy radical having 1 to 20 carbon atoms, a branched alkoxy radical having 3 to 20 carbon atoms, phenyl or benzyl, where the abovementioned radicals may be unsubstituted or substituted by halogen, in particular chlorine, bromine or fluorine, cyano, nitro, or an ester having 1 to 20 carbon atoms.

Preference is furthermore given to compounds of the formula (I) in which R¹ and R², independently of one another, are an unbranched alkoxy radical having 1 to 10 carbon atoms, a branched alkoxy radical having 3 to 20 carbon atoms, or phenyl, which may be substituted by one or more branched or unbranched alkyl or alkoxy groups having up to 20 carbon atoms.

R³ is preferably n-, i-, s- or t-butyl, i-pentyl, octyl, 3,6,9-trioxadecyl, 2-hydroxyethyl or 2-chloroethyl, particularly n-butyl or n-octyl.

The process according to the invention is equally preferably used for the preparation of compounds of the formula (I) in which Ar is the structural unit

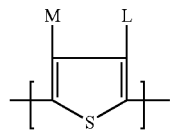

in which

M and L are identical or different and are hydrogen, an unbranched alkyl or alkoxy radical having 1 to 16 carbon atoms, a branched alkyl or alkoxy radical having 3 to 16 carbon atoms, phenyl or benzyl, where the abovementioned radicals may be unsubstituted or substituted by halogen, in particular chlorine, bromine or fluorine, cyano, nitro, or an ester having 1 to 16 carbon atoms, or M and L together are a bridge having at least 4 bridge members, which may also contain one or more heteroatoms, in particular oxygen and/or sulfur.

The reaction of the compound of the formula (II) with a sulfide of the formula (III) with formation of the bissulfonium salt of the formula (IV) is described, for example, in P. L. Burn, D. D. Bradley, R. H. Friend, D. A. Halliday, A. B. Holmes, J. Chem. Soc. Perkin Trans. 1,23,1992, 3225; P. L. Burn et al., J. Amer. Chem. Soc., 115, 22, 1993, 10117; Lee et al., Mol. Cryst. Liq. Cryst. Sci. Technol. Sect. A, 247, 1994, 121; D. Hwang, J. Chem. Soc. Chem. Commun. 21, 1994, 2461; J. Jin et al., J. Chem. Soc. Chem. Commun. 17, 1989, 1205; J. D. Stenger-Smith et al., J. Org. Chem. 59, 20, 1994, 6107; Hwang, C. Yoon, K. Moon, H. Shim, Mol. Cryst. Liq. Cryst. Sci. Technol. Sect. A, 280, 1996, 39 and 175 and 181; A. Luettringhaus, H. Machatzke, Arzneimittel Forsch. 13, 1963, 366; Bardsley, Ashford, Biochem. J. 128, 1972, 253–6; Luettringhaus, H. Machatzke, Justus Liebigs Ann. Chem. 671, 1964, 165–196; G. M. Brooke, S. D. Mawson, J. Fluorine Chem. 50, 1, 1990, 101; S. Antoun, Collect. Czech. Chem. Commun. 52, 1, 1987, 162; and Y. Sonoda, K. Kaeriyama, Bull. Chem. Soc. Jpn. 65, 3, 1992, 853.

The organic sulfide of the formula (III) is preferably dimethyl sulfide, diethyl sulfide, 2-ethylthioethanol, thiobisethanol, or a cyclic sulfide, such as tetrahydrothiopyran (=pentamethylene sulfide) or tetrahydrothiophene (THT). Particular preference is given to tetrahydrothiophene (THT).

The reaction is usually carried out in solvents, such as methanol, water, ethanol, acetone, dioxane, tetrahydropyran, tetrahydrofuran or acetonitrile, mixtures frequently also being advantageous, at temperatures between room temperature (20° C.) and the boiling point of the mixture (about 100° C.), preferably between 20° and 60° C.

From 2 to 8 equivalents of the sulfide of the formula (III) are employed per mole of the starting compound of the formula (II). About 5 equivalents are preferably employed. In the subsequent reaction step (b), the bissulfonium salt of the formula (IV) is reacted with a mercaptan of the formula (V).

The reaction is carried out in the presence of a base, where from 0.85 to 1.1 equivalents, in particular from 0.9 to 1.05 equivalents, of base are added per mole of bissulfonium salt. Suitable bases are inorganic and organic bases. Suitable inorganic bases are NaOH, KOH and LiOH. Suitable organic bases are, in particular, sterically hindered bases, such as lithium diisopropylamide (LDA), sodium trimethylsilanoate, bis(trimethylsilyl)potassium amide, but in particular alkali metal tert-butoxides, such as KOtBu and NaOtBu.

From 0.85 to 1.1 equivalents, in particular from 0.95 to 1.05 equivalents, of mercaptan of the formula (V) are employed per mole of bissulfonium salt of the formula (IV). The reaction is advantageously carried out at temperatures of between 0° and 40° C., particularly preferably at below room temperature (about 10° C.). The reaction is carried out in the presence of a polar, protic solvent. Suitable solvents are ethanol, n- and i-propanol, n-, i-, sec- and tert-butanol and mixtures, in particular methanol.

The reaction mixture is subsequently neutralized, concentrated, if necessary freed from solid and diluted with a non-polar, aprotic organic solvent whose boiling point is above that of the abovementioned polar, protic solvent. The relatively low-boiling fraction comprising polar, protic solvent and sulfide is subsequently removed, for example by evaporation under reduced pressure or by other suitable measures. By repeating this operation, the sulfide of the formula (III) is removed from the equilibrium and replaced by the leaving group X.

The concentrated solution which remains also contains, besides the compound of the formula (VI), the two possible by-products of the formula (A)

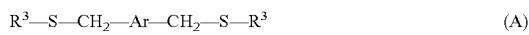

$$R^3-S-CH_2-Ar-CH_2-S-R^3 \quad (A)$$

and of the formula (B)

$$X-CH_2-Ar-CH_2-X \quad (B).$$

Surprisingly, the proportion of by-products of the formulae (A) and (B) is not as expected 25% of theory each, but is significantly lower. The detected proportion of compounds of the formulae (A) and (B) is, surprisingly, less than 15% and frequently only 5%.

The compound of the formula (VII) obtained in this way is subsequently oxidized to the sulfoxide by methods known from the literature (J. March, Adv. Org. Chem., 3rd Edn., J. Wiley, New York, pp. 1089–90).

Preference is given to a catalytic oxidation using peroxides, in particular hydrogen peroxide. Examples of suitable catalysts are $SeO_2$ and $TeO_2$. Air or oxygen can also advantageously be employed with catalytic amounts of $NO_2$.

The target compound of the formula (I) can advantageously be isolated by recrystallization from low-boiling solvents, such as alkanes, alcohols, ketones, ethers or esters. Complex chromatographic purification is unnecessary owing to the high selectivity of the process according to the invention.

The present invention furthermore relates to the compounds of the formula (VI)

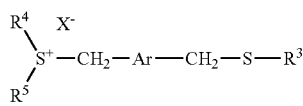

in which Ar, $R^3$, $R^4$, $R^5$ and X are as defined above.

The compounds of the formula (VI) are valuable intermediates in the synthesis of compounds of the formula (I) and can be isolated if desired.

EXAMPLES

Example 1 p-Xylylenebis(tetrahydrothiophenium chloride)

A solution of 52.5 g (0.3 mol) of p-xylylene dichloride in 105 ml (1.19 mol) of tetrahydrothiophene and 105 ml of methanol was stirred for 60 hours at room temperature. The reaction mixture was stirred into 420 ml of acetone at −10° C. The hygroscopic precipitate was rinsed with 600 ml of cold acetone and dried. 95.9 g, 91%.

Example 2 p-(Octylthiomethyl)benzyl chloride 1.83 g (19 mmol) of sodium t-butoxide and 2.78 g (19 mmol) of octanethiol were stirred into 40 g of methanol at room temperature. After 30 minutes, the clear solution was added in one portion to 6.68 g (19 mmol) of the p-xylylenebis(tetrahydrothiophenium chloride) obtained in accordance with Example 1, in 100 g of methanol. After one hour, the mixture was neutralized using 1N hydrochloric acid, and all the volatile components were removed under reduced pressure. The crude product was taken up in 200 ml of chloroform, the undissolved constituents were filtered off, and the filtrate was evaporated under reduced pressure. The oil was mixed with twice the volume of octane, and distilled off under reduced pressure together with tetrahydrothiophene. This sequence was repeated three times with octane, finally giving 5.31 g, consisting of 90% of product, 5% of starting material and 5% of p-bis(octylthiomethyl)benzene. This reaction was carried out at various temperatures and the product distribution analyzed by $^1$H-NMR spectroscopy (all data in mol-%).

| Temp./° C. | Starting material | Product | p-Bis(octylthiomethyl)-benzene |
|---|---|---|---|
| −20 | 8 | 84 | 8 |
| 0 | 6 | 87 | 7 |
| 20 | 5 | 90 | 5 |
| 40 | 6 | 87 | 7 |

Repetition of the experiments at 20° C., but with a slightly less than the stoichiometric amount of the mercaptan, gave the following product distribution:

| RSH equivalents | Starting material | Product | p-Bis(octylthiomethyl)-benzene |
|---|---|---|---|
| 0.95 | 14 | 78 | 8 |
| 0.98 | 8 | 84 | 8 |
| 1.00 | 5 | 90 | 5 |

Comparative Example A p-(Octylthiomethyl)benzyl chloride

A solution of 14.3 g (0.10 mol) of octanethiol in 100 ml of toluene was added dropwise at room temperature over the course of 24 hours to a stirred mixture of 39.4 g (0.225 mol) of p-xylylene dichloride in 400 ml of toluene, 23.7 g (0.59 mol) of NaOH in 400 ml of water and 1 g of Aliquat 336 as phase-transfer catalyst. The separated-off organic layer was washed three times with 200 ml of water each time, dried and evaporated under reduced pressure. 32.0 g, which, according to ¹H-NMR spectroscopy, consisted of 39% of product, 59% of starting material and 2% of p-bis(octylthiomethyl)benzene.

Repetition of the experiment, but without an excess of the p-xylene dichloride, gave the following product distribution:

| RSH equivalents | Starting material | Product | p-Bis(octylthiomethyl)-benzene |
|---|---|---|---|
| 1.00 | 19–25 | 50–63 | 18–25 |
| 0.45 | 70 | 28 | 2 |

Comparative Example B p-(Octylthiomethyl)benzyl chloride 1.83 g (19 mmol) of sodium t-butoxide and 2.78 g (19 mmol) of octanethiol were stirred into 40 g of methanol at room temperature. After 30 minutes, the clear solution was added in one portion to 3.33 g (19 mmol) of p-xylylene dichloride in 100 g of methanol. After one hour, the mixture was neutralized using 1N hydrochloric acid, and all the volatile components were removed under reduced pressure. The crude product was taken up in 250 ml of chloroform and washed twice with 100 ml of water each time, dried and evaporated under reduced pressure. 5.29 g, which, according to ¹H-NMR-spectroscopy, consisted of 50% of product, 25% of starting material and 25% of p-bis(octylthiomethyl)benzene.

Example 3 p-(Butylsulfinylmethyl)benzyl chloride

A solution of 17.1 g (178 mmol) of sodium t-butoxide and 19.4 ml (16.4 g, 181 mmol) of butanethiol in methanol was added to a clear solution of 67.1 g of the bissulfonium salt prepared in accordance with Example 1 in 300 ml of methanol. After 30 minutes, the solvent was removed, and octane was added and distilled off. This last sequence was repeated three times. The oil which remained was taken up in chloroform, washed with water and sodium hydrogencarbonate solution, dried over magnesium sulfate and filtered, which also removed undissolved organic residues. Hydrogen peroxide was added to a solution of this intermediate in 50 ml of 1,4-dioxane, 250 ml of methanol and tellurium dioxide. After five hours, 100 ml of saturated sodium chloride solution were added, and the mixture was extracted with chloroform and dried, giving 43.4 g of p-(butylsulfinylmethyl)benzyl chloride.

Recrystallization from 800 ml of acetone followed by crystallization from chloroform/hexane gave 40 g of the product in extremely high purity. ¹H-NMR spectroscopy only showed impurities at the level of ¹³C satellites.

Example 4

2-(3,7-Dimethyloctyloxy)-5-methoxyxylylene-1,4-bis(tetrahydrothiophenium chloride)

10 g (27.7 mmol) of 1,4-bischloromethyl-2-(3,7-dimethyloctyloxy)-5-methoxybenzene (BCDM) and 12.4 g (141 mmol) of tetrahydrothiophene (THT) were dissolved in 20 ml of methanol at 30° C. After 70 hours, excess THT was distilled off, and the residue was dissolved in just sufficient methanol, filtered and stirred into 100 ml of ice-cold acetone. The solid was digested with 40 ml of hexane. Drying for 4 hours under reduced pressure gave 11 g (72% of theory).

Example 5

2-(3,7-Dimethyloctyloxy)-5-methoxy-4-butylthiomethylbenzyl chloride via 2-(3,7-dimethyloctyloxy)-5-methoxy-4-butylthiomethylbenzyl tetrahydrothiophenium chloride, each as a mixture of the regioisomers 6.5 g (68 mmol) of sodium t-butoxide (1 eq.) and 6.0 g (66.5 mmol, 0.98 eq,) of butanethiol (BuSH) were stirred into 150 ml of methanol at 20° C. After 30 minutes, the clear solution was added dropwise to a solution of 37.6 g (68 mmol, 1 eq.) of the salt prepared in accordance with Example 4 in 400 ml of methanol. After a reaction time of 60 minutes at 20° C., the mixture was neutralized using 1N hydrochloric acid, after which all the volatile components were distilled off under reduced pressure. The residue was taken up in 200 ml of chloroform and filtered. The filtrate was concentrated under reduced pressure, and the resultant oil was taken up in 80 ml. After the mixture of octane and THT had been evaporated, this procedure was repeated three times. Yield 39.5 g, consisting of 18% of BCDM, 7% of bisthioether and 74% of the desired product as a 50:50 mixture of the two regioisomers 2-(3,7-dimethyloctyloxy)-5-methoxy-4-butylthiomethylbenzyl chloride and 5-(3,7-dimethyloctyloxy)-2-methoxy-4-butylthiomethylbenzyl chloride. The two regioisomers were also isolated by preparative column chromatography.

Example 6

Example 5 was repeated with the following modifications:

a. reaction time of 40 instead of 60 minutes b. 1.1 equivalents of NaOtBu instead of 1 eq.

c. 0.99 equivalent of BuSH instead of 0.98 eq.

16% of BCDM, 7% of bisthioether and 77% of the desired product as a 49:51 mixture of the two regioisomers, and slight traces of the polymer undesired here, were obtained.

Example 7

39.59 of the product from Example 5 were dissolved in 200 ml of dioxane, and 1.82 g (11.4 mmol, 12 mol-%) of tellurium dioxide were added. 18.5 g (190 mmol) of a 35% strength aqueous hydrogen peroxide solution were added dropwise at room temperature with vigorous stirring. As soon as a trace of the sulfone, as a sign of overoxidation, was detectable by thin layer chromatography, (3.5 hours), the reaction was terminated by pouring in ice-water. The aqueous phase was extracted with three portions of chloroform (250, 100 and 100 ml). After drying, the combined organic phases gave 30 g of the product: 76% of the desired regioisomer 2-(3,7-dimethyloctyloxy)-5-methoxy-4-butylsulfinylmethylbenzyl chloride and 5-(3,7-dimethyloctyloxy)-2-methoxy-4-butylsulfinylmethylbenzyl chloride, 16% of BCDM and 7% of the bis(butylsulfinyl) derivative.

This mixture can successfully be employed for polymerization even without purification.

Example 8

Example 5 was repeated with the reaction temperature lowered from 20° to 10° or 0° C. The following product distribution was found:

| Temp./° C. | BCDM | Bisbutylthio derivative | Product (regioisomers) |
|---|---|---|---|
| 20 | 18 | 7 | 74 (50:50) |
| 10 | 19 | 4 | 77 (51:49) |
| 0 | 17 | 4 | 79 (51:49) |

Example 9

2,5-Dimethylxylylene dichloride (9a),
2,5-dimethoxyxylylene dichloride (9b) and
2,5-dichloroxylylene dichloride (9c)

were prepared in accordance with Example 5, where, owing to the improved solubility, methanol or mixtures with water were selected as solvent in the reaction with BuSH:

| Example | MeOH:H$_2$O | Starting material | Product | Bis(butylthio)xylene derivative |
|---|---|---|---|---|
| 9a | 1:0 | 9 | 86 | 5 |
| 9b | 1:0 | 8 | 80 | 12 |
| 9c | 4:1 | 7 | 86 | 7 |

4-Butylthiomethyl-2,5-dicyanobenzyl chloride can be prepared in an analogous manner in acetonitrile:water (65:35). 2-Butylthiomethyl-2-chloromethylnaphthalene was obtained in anhydrous methanol.

Comparative Experiment p-Phenylsulfinylmethylbenzyl chloride 3.8 ml (37.8 mmol) of thiophenol were dissolved in 100 ml of dry tetrahydrofuran (THF), and 0.91 g (37.8 mmol) of NaH were slowly added. The suspension was added dropwise to a vigorously stirred solution, at 25° C., of 33.08 g (189 mmol, i.e. a five-fold excess) of p-bischloromethyl-benzene in 150 ml. After 14 hours, 100 ml of water were added, and the mixture was extracted four times with 50 ml of chloroform each time. The combined organic extracts were dried over magnesium sulfate, and the solvent was evaporated, ultimately under reduced pressure.

The crude mixture, consisting of p-bischloromethylbenzene, p-(bisphenylthiomethyl)benzene and the desired p-phenylthiomethylbenzyl chloride, was subjected, without further purification, to oxidation to the sulfoxide: The mixture was dissolved in 450 ml of methanol together with 0.6 g (0.037 mmol) of TeO$_2$. 8.6 ml of 30% strength by weight hydrogen peroxide (76 mmol) were added dropwise with vigorous stirring. 4 hours later, 100 ml of water were added, the aqueous phase was extracted with chloroform, dried as usual using magnesium sulfate and evaporated to dryness. The crude product (30 g) was purified by chromatography over silica gel (300 g). After recrystallization from hexane/toluene, 5.5 g of p-phenylsulfinylmethylbenzyl chloride were obtained as colorless crystals. The yield is 55% based on thiophenol, but only 11% based on the bischloromethyl compound (5-fold excess).

The invention claimed is:

1. A process for the preparation of compounds of the formula (I):

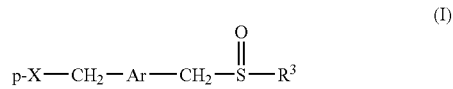

in which:

Ar is an optionally substituted aromatic ring system having 4 to 20 carbon atoms, X is a leaving group, R$^3$ is unbranched alkyl having 1 to 20 carbon atoms, branched alkyl having 3 to 20 carbon atoms, cyclic alkyl, C$_1$–C$_4$-alkyl-substituted cyclic alkyl, phenyl, or benzyl, which is optionally substituted or unsubstituted, and optionally contains at least one heteroatom, and p denotes para with respect to the two methylene radicals on both sides of Ar, the process comprising the following steps:

a) reacting a compound of the formula (II):

in which Ar and X are as defined under the formula (I), with an organic sulfide of the formula (III):

in which:

R$^4$ and R$^5$ are identical or different and are unbranched alkyl having 1 to 20 carbon atoms, branched alkyl having 3 to 20 carbon atoms, cyclic alkyl having 3 to 10 carbon atoms, or C$_1$–C$_4$-alkyl-substituted cyclic alkyl, or R$^4$ and R$^5$ together form a ring, which optionally contains at least one heteroatom selected from the group consisting of oxygen, sulfur, and nitrogen, to give a compound of the formula (IV):

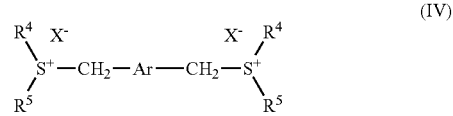

in which R$^4$, R$^5$, X, and Ar are as defined above, b) reacting the compound of the formula (IV) with from 0.85 to 1.1 equivalents of a mercaptan of the formula (V):

in which:

R$^3$ is unbranched alkyl having 1 to 20 carbon atoms, branched alkyl having 3 to 20 carbon atoms, cyclic alkyl, C$_1$–C$_4$-alkyl-substituted cyclic alkyl, phenyl, or benzyl, which optionally is substituted or unsubstituted and optionally contains at least one heteroatom, to give a compound of the formula (VI):

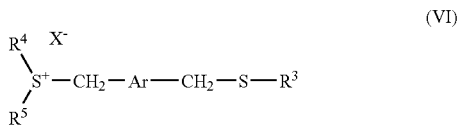 (VI)

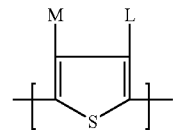

c) warming of the compound of the formula (VI) in a liquid and formation of the compound of the formula (VII):

 (VII)

by elimination of the organic sulfide of the formula (III), where the compound of the formula (VII) is dissolved in the above liquid, d) oxidizing the compound of the formula (VII) with an oxidant, to give the compound of the formula (I).

2. The process as claimed in claim 1, wherein Ar is an aromatic ring that is mono- or polysubstituted by $C_1$–$C_{20}$-alkyl, $C_3$–$C_{20}$-alkoxy, $C_3$–$C_{20}$-branched alkyl, phenyl or benzyl radicals, and optionally contains up to 4 heteroatoms selected from the group consisting of oxygen, sulfur, and nitrogen.

3. The process as claimed in claim 1, wherein $R^3$ is cyclohexyl or cyclohexylmethyl.

4. The process as claimed in claim 1, wherein $R^3$ contains at least one heteroatom selected from the group consisting of O, N, and Si.

5. The process as claimed in claim 1, wherein $R^4$ and $R^5$ are independently selected from the group consisting of cyclobutyl, cyclopentyl, cyclohexyl, and cyclohexylmethyl.

6. The process as claimed in claim 1, wherein the radical X is selected from the group consisting of halogen, —O-tosylate, —O-mesylate, and —O-trifluoroacetate.

7. The process as claimed in claim 1 wherein Ar is the structural unit:

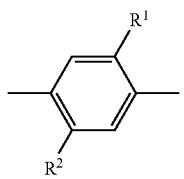

in which:

$R^1$ and $R^2$ are identical or different and are hydrogen, an unbranched alkyl or alkoxy radical having 1 to 20 carbon atoms, a branched alkyl or alkoxy radical having 3 to 20 carbon atoms, phenyl, or benzyl, where the abovementioned radicals are optionally substituted by halogen, cyano, nitro, or an ester having 1 to 20 carbon atoms.

8. The process as claimed in claim 7, wherein the alkoxy radical is substituted by a halogen selected from the group consisting of chlorine, bromine, and fluorine.

9. The process as claimed in claim 1, wherein Ar is the structural unit:

in which:

M and L are identical or different and are hydrogen, an unbranched alkyl or alkoxy radical having 1 to 16 carbon atoms, a branched alkyl or alkoxy radical having 3 to 16 carbon atoms, phenyl or benzyl, where the abovementioned radicals are optionally substituted by halogen, cyano, nitro, or an ester having 1 to 16 carbon atoms, or M and L together are a bridge having at least 4 bridge members, which optionally contains at least one heteroatom.

10. The process as claimed in claim 9, wherein the alkoxy radical is substituted by a halogen selected from the group consisting of chlorine, bromine, and fluorine.

11. The process as claimed in claim 9, wherein M and L form a bridge having at least 4 bridge members and the bridge contains at least one heteroatom selected from the group consisting of oxygen and sulfur.

12. The process as claimed in claim 7, wherein $R^1$ and $R^2$, independently of one another, are an unbranched alkoxy radical having 1 to 20 carbon atoms, a branched alkoxy radical having 3 to 20 carbon atoms, phenyl or benzyl, where the abovementioned radicals optionally are substituted by halogen, cyano, nitro, or an ester having 1 to 20 carbon atoms.

13. The process as claimed in claim 12, wherein the branched alkoxy radical is substituted by a halogen selected from the group consisting of chlorine, bromine, or fluorine.

14. The process as claimed in claim 12, wherein $R^1$ and $R^2$, independently of one another, are an unbranched alkoxy radical having 1 to 10 carbon atoms, a branched alkoxy radical having 3 to 20 carbon atoms, or phenyl, which optionally is substituted by one or more branched or unbranched alkyl or alkoxy groups having up to 20 carbon atoms.

15. The process as claimed in claim 1, wherein $R^3$ is n-, i-, s-, or t-butyl, i-pentyl, octyl, 3,6,9-trioxadecyl, 2-hydroxyethyl, or 2-chloroethyl.

16. The process as claimed in claim 1, wherein the organic sulfide of the formula (III) is dimethyl sulfide, diethyl sulfide, 2-ethylthioethanol, thiobisethanol, or a cyclic sulfide.

17. The process as claimed in claim 1, wherein the organic sulfide of the formula (III) is tetrahydrothiopyran or tetrahydrothiophene.

18. The process as claimed in claim 1, wherein the reaction in step a) is carried out in methanol, water, ethanol, acetone, dioxane, tetrahydropyran, tetrahydrofuran, acetonitrile, or a mixture thereof.

19. The process as claimed in claim 1, wherein the reaction in step a) is carried out at a temperature of from about 20° C. to 100° C.

20. The process as claimed in claim 1, wherein the reaction in step a) is carried out at a temperature of from about 20° C. to 60° C.

21. The process as claimed in claim 1, wherein the reaction in step b) is carried out in the presence of a base.

22. The process as claimed in claim 1, wherein from 0.95 to 1.05 equivalents of mercaptan of the formula (V) are employed per mole of the compound of the formula (IV).

23. The process as claimed in claim 1, wherein the reaction in step b) is carried out at a temperature of from 0° C. to 40° C.

24. The process as claimed in claim 1, wherein the reaction in step b) is carried out in a polar, protic solvent.

25. A compound of the formula (VI):

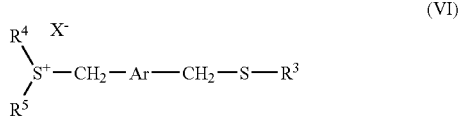

(VI)

in which:
Ar is an optionally substituted aromatic ring system having 4 to 20 carbon atoms,
X is a leaving group,
$R^3$ is unbranched alkyl having 1 to 20 carbon atoms, branched alkyl having 3 to 20 carbon atoms, cyclic alkyl, $C_1$–$C_4$-alkyl-substituted cyclic alkyl, phenyl, or benzyl, which optionally is substituted and optionally contains at least one heteroatom, and
$R^4$ and $R^5$ are identical or different and are unbranched alkyl having 1 to 20 carbon atoms, branched alkyl having 3 to 20 carbon atoms, cyclic alkyl having 3 to 10 carbon atoms, or $C_1$–$C_4$-alkyl-substituted cyclic alkyl, or $R^4$ and $R^5$ together form a ring, which optionally contains at least one heteroatom selected from the group consisting of oxygen, sulfur, and nitrogen.

26. The compound as claimed in claim 1, wherein Ar is an aromatic ring that is mono- or polysubstituted by $C_1$–$C_{20}$-alkyl, $C_3$–$C_{20}$-alkoxy, $C_3$–$C_{20}$-branched alkyl, phenyl or benzyl radicals, and optionally contains up to 4 heteroatoms selected from the group consisting of oxygen, sulfur, and nitrogen.

27. The compound as claimed in claim 25, wherein $R^3$ is cyclohexyl or cyclohexylmethyl.

28. The compound as claimed in claim 25, wherein $R^3$ contains at least one heteroatom selected from the group consisting of O, N, and Si.

29. The compound as claimed in claim 25, wherein $R^4$ and $R^5$ are independently selected from the group consisting of cyclobutyl, cyclopentyl, cyclohexyl, and cyclohexylmethyl.

30. The compound as claimed in claim 25, wherein Ar is the structural unit

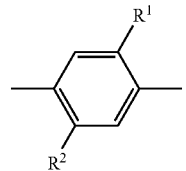

in which:
$R^1$ and $R^2$ are identical or different and are hydrogen, an unbranched alkyl or alkoxy radical having 1 to 20 carbon atoms, a branched alkyl or alkoxy radical having 3 to 20 carbon atoms, phenyl or benzyl, where the abovementioned radicals optionally are substituted by halogen, cyano, nitro, or an ester having 1 to 20 carbon atoms.

31. The compound as claimed in claim 30, wherein the alkoxy radicals are substituted by a halogen selected from the group consisting of chlorine, bromine, and fluorine.

32. The compound as claimed in claim 25, wherein Ar is the structural unit

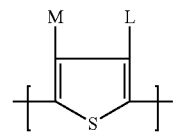

in which:
M and L are identical or different and are hydrogen, an unbranched alkyl or alkoxy radical having 1 to 16 carbon atoms, a branched alkyl alkoxy radical having 3 to 16 carbon atoms, phenyl or benzyl, where the abovementioned radicals optionally are substituted by halogen, cyano, nitro, or an ester having 1 to 16 carbon atoms, or M and L together are a bridge having at least 4 bridge members, which optionally contains at least one heteroatom.

33. The compound as claimed in claim 32, wherein the alkoxy radical is substituted by a halogen selected from the group consisting of chlorine, bromine, and fluorine.

34. The compound as claimed in claim 32, wherein M and L form a bridge having at least 4 bridge members and the bridge contains at least one heteroatom selected from the group consisting of oxygen and sulfur.

* * * * *